United States Patent
Cornille et al.

(10) Patent No.: US 6,603,016 B2
(45) Date of Patent: *Aug. 5, 2003

(54) PROCESS FOR THE PREPARATION OF N-CARBOXYANHYDRIDES

(75) Inventors: Fabrice Cornille, Bures S/Yvette (FR); Marc Lebon, Ormoy la Riviere (FR)

(73) Assignee: Isochem, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/158,712

(22) Filed: May 30, 2002

(65) Prior Publication Data

US 2002/0183551 A1 Dec. 5, 2002

(30) Foreign Application Priority Data

May 31, 2001 (FR) .............................................. 01 07140

(51) Int. Cl.$^7$ ............................................. C07D 263/44
(52) U.S. Cl. ........................ 548/227; 548/229; 560/24
(58) Field of Search ................................ 548/229, 227; 560/24

(56) References Cited

U.S. PATENT DOCUMENTS 6,479,665 B2 * 11/2002 Cornille et al. ............. 548/227

FOREIGN PATENT DOCUMENTS

GB            1038913     *  8/1966   ......... C07C/101/20

OTHER PUBLICATIONS

Theodora W. Greene, 1982, Wiley–Interscience Publication, "Protective Groups in Organic Synthesis", 152–192, and 218–287.*

* cited by examiner

Primary Examiner—Ceila Chang
Assistant Examiner—Robert Shiao
(74) Attorney, Agent, or Firm—Bucknam and Archer

(57) ABSTRACT

The invention relates to an improved process for the preparation of N-carboxyanhydrides by reaction of the corresponding amino acid or one of its salts with phosgene, diphosgene and/or triphosgene in a solvent medium, characterized in that at least a portion of the reaction is carried out under a pressure of less than 1000 mbar. The N-carboxyanhydrides are thus obtained with better yields and an improved purity.

10 Claims, No Drawings

PROCESS FOR THE PREPARATION OF N-CARBOXYANHYDRIDES

The invention relates to an improved process for the preparation of N-carboxyanhydrides from the corresponding amino acids and phosgene, diphosgene or triphosgene.

The N-carboxyanhydrides (abbreviation NCA) obtained from α-, β- or γ-amino acids are very useful compounds because of the activation of their acid functional group. In fact, they make it possible to react this acid functional group with any nucleophilic entity. Thus, the preparation of the amide functional group by reaction with an amine functional group is facilitated. For this reason, they readily polymerize and are used to form peptides. The ester bond, by reaction with an alcohol, is also easily created. They are also advantageous when it is desired to reduce an acid functional group.

Several processes are known for preparing N-carboxyanhydrides. One of the most widespread and most direct is the process according to which an amino acid or its hydrochloride is reacted with phosgene, diphosgene or triphosgene in a solvent medium.

The general reaction scheme with phosgene is as follows:

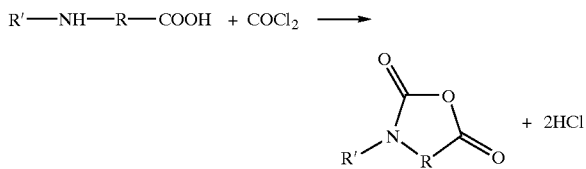

in which R represents the main radical of the α-, β- or γ-amino acid and R' represents a hydrogen atom or the radical of the secondary amino group of the amino acid, it being possible for R' to form a ring with R.

It is found that, in addition to the N-carboxyanhydride, a large amount of hydrochloric acid is also formed, that is to say 2 mol per mole of NCA. Hydrochloric acid is very reactive. Its presence in the medium leads to side reactions and to the appearance of chlorinated by-products. These chlorinated impurities, which remain in the NCA produced, are entirely undesirable, both in terms of quality and in terms of yield. This is because they are extremely harmful to the polymerization reaction of the NCA. In order for this polymerization to be carried out appropriately, it is necessary for the amount of chlorinated compounds present in the NCA monomers to be sufficiently low. Thus, the level of hydrolysable chlorine should generally be less than 0.05% by weight.

In point of fact, according to the known processes, when the reaction is carried out without the presence of a basic compound, it is difficult to reproducibly obtain such a low level of hydrolysable chlorine. On the other hand, when a basic compound is added to neutralize the hydrochloric acid, the polymerization of the NCA, which is not desired at this stage, is activated and there is then a risk of it occurring in the medium.

Furthermore, one of the other difficulties of the prior processes is the choice of the solvent. This is because it has been found that, in solvents such as aliphatic esters, for example ethyl acetate, or nonpolar aprotic solvents, such as dichloromethane or toluene, the reaction for the formation of the NCA is generally very slow and incomplete. In a solvent of the family of the ethers, such as tetrahydrofuran or dioxane, the reaction is faster but these solvents are not completely inert with respect to phosgene and hydrochloric acid, which generates other impurities.

There consequently existed a need to improve the existing process, in which the amino acid is reacted directly with phosgene, diphosgene or triphosgene, in order to obtain NCA with better yields and an improved purity, possessing in particular a level of hydrolysable chlorine of less than 0.05%. The decrease in the duration of the reaction, in the most inert solvents, was also highly desirable.

The process according to the present invention meets these needs. This process is characterized in that, to prepare the N-carboxyanhydrides, the reaction of the corresponding α-, β- or γ-amino acid or one of its salts with phosgene, diphosgene and/or triphosgene, in a solvent medium, is carried out at least partly under a pressure of less than 1000 mbar ($10^5$ Pa).

This novel process makes it possible to solve the problems which were posed in the implementation of the processes of the prior art. A portion of the hydrochloric acid is thus removed from the reaction medium as it is formed. The numerous side reactions brought about by it are suppressed and, consequently, the appearance of the harmful impurities also. Furthermore, the shifting of the reaction equilibrium in the direction of the production of the desired NCA is also promoted and the kinetics of the reaction are then accelerated.

It has also been found that, in the case of the conversion of amino acids with a secondary amine functional group, the implementation of this reaction under this reduced pressure renders unnecessary the addition, to the medium, of a tertiary amine, such as triethylamine or N-methylmorpholine. Such an amine was nevertheless until now regarded as necessary by a person skilled in the art for carrying out the or in part, in a linear or branched and substituted or unsubstituted alkyl radical and/or in a substituted or unsubstituted alkyl or heteroalkyl ring. The substituents are the groups or atoms which are generally found in amino acids, such as, for example, hydroxyl, caboxyl, mercapto, alkylthio, alkyldithio, alkyl, cycloalkyl, heterocycloalkyl, aryl, heteroaryl, alkyloxy or aryloxy groups, halogen atoms, such as fluorine, chlorine, bromine or iodine atoms, or amino, guanidino or amido groups, which may or may not be substituted by alkyl groups.

More specifically, in the amino acids under consideration, the alkyl groups comprise from 1 to 7 carbon atoms and are substituted or are not substituted by the substituents indicated above. The aryl groups are unsubstituted or are substituted by substituents chosen from halogen atoms, such as fluorine, chlorine, bromine or iodine atoms, and alkyl, alkoxy, aryloxy, aryl, mercapto, alkylthio, hydroxyl, carboxyl, amino, alkylamino, dialkylamino, nitro or trifluoromethyl groups. When they are present, these substituent groups more particularly number from one to three. The aryl groups are in particular the substituted or unsubstituted phenyl or naphthyl radicals.

The cycloalkyl groups are composed of rings having from 3 to 7 carbon atoms which are substituted or unsubstituted. The heterocycles, which may or may not be substituted, are cycloalkyl or aryl groups which comprise, in the ring, at least one heteroatom chosen from the nitrogen, oxygen or sulphur atom.

The substituents of the cycloalkyl or heterocycloalkyl groups are chosen from the substituents indicated above for the alkyl and aryl radicals. The substituents of the heteroaryl groups are chosen from the substituents indicated for the aryl groups.

The heteroaryl groups are preferably substituted or unsubstituted 2- or 3-furanyl, 2- or 3-thienyl, 2-, 3- or 4-pyridinyl, 4-imidazolyl and 3-indolyl groups.

The amino acids can be in their various forms and in particular, when they possess one or more asymmetric carbons, in their various enantiomeric forms, mixtures, either racemic or of diastereoisomers, or in the form of pure stereoisomers.

When the radical of the amino acid comprises functional groups, other than the amino group and the acid group forming the anhydride ring, capable of reacting under the conditions of the process, they are masked by protective groups in a known way.

The reactive amino group can be a primary or secondary amino group. Consequently, the nitrogen atom can carry a substituted or unsubstituted aliphatic, cyclo-aliphatic, araliphatic or aryl radical, as is usual for the class of the amines. In particular, this radical can be substituted by the groups indicated above as substituents.

The radical of the amino group can also form a ring, unsubstituted or substituted as indicated above, with the residue of the radical of the amino acid, such as, for example, in proline.

When the radical of the amino group comprises reactive groups other than the acid group and the amino group forming the anhydride, they are protected conventionally.

Mention may in particular be made, as radical of this amino group, of alkyl, cycloalkyl or aralkyl groups which are unsubstituted or substituted, for example by groups as disclosed in U.S. Pat. No. 4,686,295, for the novel NCA formed by means of phosgene, in particular substituted by one or more groups chosen from alkoxycarbonyl, aryloxycarbonyl and aralkyloxycarbonyl groups.

Mention may be made, as examples of amino acids, of the commonest amino acids, such as glycine, alanine, valine, leucine, isoleucine, phenylalanine, serine, threonine, lysine, δ-hydroxylysine, arginine, ornithine, aspartic acid, asparagine, glutamic acid, glutamine, cysteine, cystine, methionine, tyrosine, thyroxine, proline, hydroxyproline, tryptophan, histidine and their derivatives.

It is possible to use, in place of the amino acid, one of its salts as starting compound. The term "salts of the amino acid" is understood to mean the salts obtained by reaction of the amino group with organic or inorganic acids, such as, for example, the sulphates, acetates, toluenesulphonates or methanesulphonates, and preferably the hydrohalides, in particular the hydrochlorides and hydrobromides.

The hydrochlorides are the preferred salts.

The process is highly suitable for producing the N-carboxyanhydrides of amino acids such as N-(1-ethoxycarbonyl-3-phenylpropyl)alanine, leucine, alanine, N-(trifluoroacetyl)lysine, or the γ-benzyl ester or γ-methyl ester of glutamic acid.

For the implementation of the process, phosgene, diphosgene and/or triphosgene can be reacted with the amino acid to form the ring of the N-carboxyanhydride. Phosgene is the preferred compound.

A large excess of phosgene with respect to the amino acid is not necessary. Thus, preferably, approximately from 1 to 3 mol of phosgene per mole of amino acid or of its salt is added.

Diphosgene or triphosgene are added in a corresponding amount in order to obtain the same phosgene/amino acid ratios.

The reaction can be carried out in a polar aprotic solvent. Ethers, in particular tetrahydrofuran and dioxane, car be used but, preferably, a solvent belonging to the family of the aliphatic esters is chosen.

Non-polar aprotic solvents belonging to the family of the chlorinated or nonchlorinated aliphatic or aromatic hydrocarbons, for example dichloromethane or toluene, can also be used.

The solvents belonging to the family of the esters or of the hydrocarbons have the advantage of not reacting with phosgene or hydrochloric acid. Their use is consequently more advantageous.

Alkyl acetates are highly suitable and in particular ethyl acetate.

According to the invention, the reaction is at least partly carried out at a pressure of less than 1000 mbar ($10^5$ Pa) and in particular of less than or equal to 960 mbar ($96 \times 10^3$ Pa).

When the solvent is a hydrocarbon, the pressure is chosen more particularly within the range from 50 to 960 mbar. Preferably, when the solvent is ethyl acetate or a hydrocarbon, the pressure is chosen within the range from 800 to 960 mbar.

The temperature of the reaction is generally the usual temperature, of between 0° C. and 120° C. or equal to these values, and preferably of between approximately 40° C. and approximately 90° C.

The reaction is preferably carried out under anhydrous conditions.

One of the advantages of the process according to the invention is that the reaction time is shortened and can even be reduced by half with respect to that of the prior art, in particular in solvents such as esters. As the latter solvents are furthermore less expensive, the use of the process according to the invention for this reason results in a true saving.

When the reaction is complete, the products are isolated according to conventional procedures. The phosgene and the solvent are generally removed by distillation under very low pressure.

The yield of NCA obtained after crystallization is markedly improved and often greater than or equal to 90%. The level of hydrolysable chlorine is less than 0.05%.

Consequently, the NCA prepared according to the process of the invention can be used in numerous applications for which very pure products are required, in particular for the preparation of pharmaceutical products.

The examples which follow illustrate the invention without, however, limiting it.

EXAMPLE 1

Preparation of the N-carboxyanhydride of the γ-Benzyl Ester of Glutamic Acid (H-Glu(OBzl)-NCA).

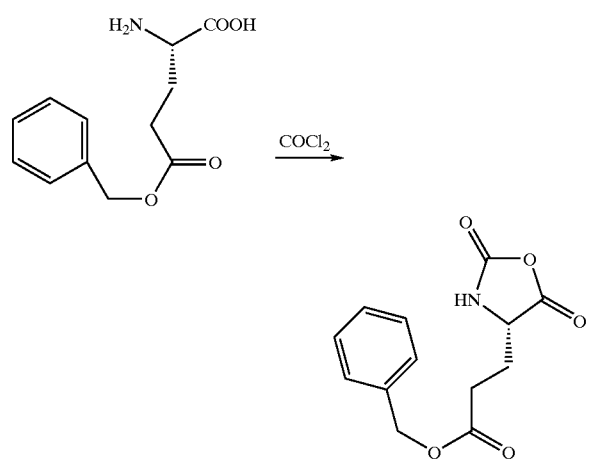

100 g (0.42 mol) of H-Glu(OBzl)-OH are suspended in 885 ml of ethyl acetate. The suspension is cooled to 5° C. and then 90 g (0.91 mol, 2.16 eq) of gaseous phosgene are introduced therein over 1 hour 30 at a temperature of 10° C.

The temperature of the reaction medium is brought to 60° C., then the reaction medium is placed under reduced pressure (850–950 mbar) and is left under stationary conditions for 3 hours at a bulk temperature of 60° C. The medium becomes clear after one hour under stationary conditions.

Distillation is subsequently carried out at approximately 13 mbar to separate 600 ml of a mixture of ethyl acetate and of phosgene. 600 ml of industrial heptane are added under warm conditions to the remaining medium and the medium is cooled at 0° C. for 1 hour. The product which crystallized is filtered off and washed with industrial heptane.

After drying, 106 g (yield: 95.5%) of H-Glu(OBzl)-NCA are obtained, the level of hydrolysable chlorine of which is less than 0.05%.

COMPARATIVE EXAMPLE 1
Preparation of the N-Carboxyanhydride of the γ-Benzyl Ester of Glutamic Acid (H-Glu(OBzl)-NCA)

100 g (0.42 mcl) of H-Glu(OBzl)-OH are suspended in 885 ml of ethyl acetate. The suspension is cooled to 5° C. and then 90 g (0.91 mol, 2.16 eq) of gaseous phosgene are introduced therein.

The reaction medium is heated to 60° C. The reaction takes place slowly. The reaction medium has to be left under stationary conditions for 6 hours at this temperature instead of 3 hours in the preceding example.

Distillation is subsequently carried out as above to separate 600 ml of a mixture of ethyl acetate and of phosgene. 600 ml of industrial heptane are added under warm conditions to the remaining medium and the medium is cooled at −10° C. for 2 hours. The product which crystallized is filtered off and washed with industrial heptane.

After drying, 88 g of H-Glu(OBzl)-NCA are obtained, the level of hydrolysable chlorine of which is 0.13%. The yield is only 74.6%.

EXAMPLE 2
Preparation of the N-Carboxyanhydride of N-(1-ethoxycarbonyl-3-phenylpropyl)alanine (EPAL-NCA).

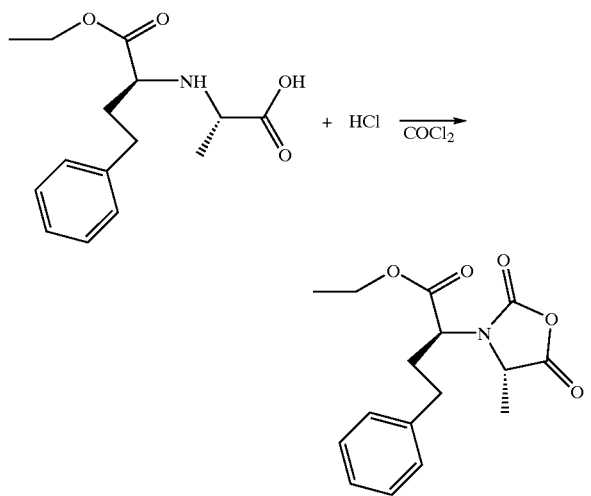

350 ml of anhydrous ethyl acetate and then 42 g (0.15 mol, 1 equivalent) of N-(1-ethoxycarbonyl-3-phenylpropyl) alanine (EPAL) are introduced into a thermostatically controlled 1 liter reactor rendered inert beforehand with nitrogen. 6 g (0.165 mol, 1.1 equivalent/EPAL) of anhydrous gaseous hydrochloric acid are then introduced over 15 minutes at a temperature of between 10° C. and 28° C. into the mechanically stirred suspension obtained in order to form EPAL hydrochloride.

30 g (0.3 mol, 2 equivalents/EPAL) of gaseous phosgene are subsequently added to the reaction medium over one hour. The medium is subsequently heated to 60° C. and the pressure is reduced to approximately 800 mbar to produce reflux of the ethyl acetate. These conditions are maintained for 3 hours. It is then found, by HPLC analysis, that there is no more EPAL in the reaction medium.

The remaining hydrochloric acid and excess phosgene are removed and the ethyl acetate is separated by lowering the pressure to approximately 13 mbar (1.3 kPa).

200 ml of diisopropyl ether are subsequently added to the concentrated reaction medium and it is cooled to 0°–5° C. The EPAL-NCA crystallizes. It is collected by filtration under a nitrogen atmosphere.

After drying under vacuum at a temperature of 20°–25° C., 41.2 g of EPAL-NCA (white solid) with a purity of greater than 99.7%, determined by HPLC, are obtained, the level of hydrolysable chlorine of which is less than 0.05%. The yield is 90%.

COMPARATIVE EXAMPLE 2
Preparation of the N-Carboxyanhydride of N-(1-ethoxycarbonyl-3-phenylpropyl)alanine (EPAL-NCA).

The same amounts of compounds as in the preceding example are used and the preparation is carried out in the same way and under the same conditions, with the exception of the pressure of the reaction, which is not reduced and which remains standard atmospheric pressure.

After reacting for eight hours at 60° C., 3.73% by weight of unreacted EPAL still remains in the reaction medium and no conversion is any longer observed.

EXAMPLE 3
Preparation of the N-Carboxyanhydride of Alanine (H-Ala-NCA).

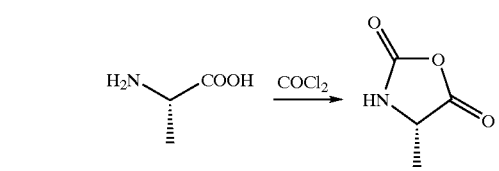

25 g (0.285 mol) of alanine (H-Ala-OH) are suspended in 220 ml of ethyl acetate. 70.5 g (0.71 mol, 2.5 eq) of gaseous phosgene are subsequently introduced into the suspension over 1 hour 30 at a temperature of 10° C.

The reaction medium is heated to 55° C., is then placed under reduced pressure (850–950 mbar) and is thus left under stationary conditions for 6 hours at a bulk temperature of 55° C. It becomes clear after 3 hours under stationary conditions.

Distillation is subsequently carried out under a very low pressure in order to separate 200 ml of a mixture of ethyl acetate and of phosgene.

80 ml of toluene are then added under warm conditions to the remaining medium and another distillation is carried out in order to separate 78 g of a mixture of ethyl acetate and of toluene. The remaining medium is subsequently cooled at 0° C. for 1 hour. The product which crystallized is filtered off and washed with 39 g of cold toluene.

After drying, 19.4 g (yield: 59.2%) of H-Ala-NCA are obtained, the level of hydrolysable chlorine of which is less than 0.05%.

What is claimed is:

1. Process for the preparation of N-carboxyanhydrides by reaction of the corresponding α-, β- or γ-amino acid or one of its salts with phosgene, diphosgene and/or triphosgene in a solvent medium, characterized in that at least a portion of the reaction is carried out under a total pressure of less than 1000 mbar.

2. Process according to claim 1, characterized in that the total pressure is less than or equal to 960 mbar.

3. Process according to claim 1, characterized in that the solvent consists of aliphatic esters.

4. Process according to claim 1, characterized in that the solvent is ethyl acetate and the total pressure is within the range from 800 to 960 mbar.

5. Process according to claim 1, characterized in that the reaction is carried out with phosgene.

6. Process according to claim 1, characterized in that, when the amino acid comprises reactive groups other than the acid group and the amino group forming the anhydride, they are protected.

7. Process according to claim 1, characterized in that the starting amino acid is chosen from the group consisting of leucine, alanine, N-(trifluoroacetyl) lysine, the γ-benzyl ester and the γ-methyl ester of glutamic acid, N-(1-ethoxycarbonyl-3-phenylpropyl)alanine and their salts.

8. Process according to claim 1, characterized in that the amino acid salt is a sulphate, an acetate, a toluenesulphonate or a methanesulphonate.

9. Process according to claim 1, characterized in that the amino acid salt is a hydrohalide.

10. Process according to claim 1, characterized in that the reaction is carried out at a temperature of between 0° C. and 120° C.

* * * * *